United States Patent
Ryu et al.

(10) Patent No.: US 11,051,518 B2
(45) Date of Patent: Jul. 6, 2021

(54) *PSEUDOZYMA CHURASHIMAENSIS* STRAIN RGJ1 ISOLATED FROM PEPPER PLANT AND USE THEREOF

(71) Applicant: KOREA RESEARCH INSTITUTE OF BIOSCIENCE AND BIOTECHNOLOGY, Daejeon (KR)

(72) Inventors: Choong-Min Ryu, Daejeon (KR); Ga-Hyung Lee, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 69 days.

(21) Appl. No.: 16/312,035

(22) PCT Filed: Jun. 27, 2016

(86) PCT No.: PCT/KR2016/006818
§ 371 (c)(1),
(2) Date: Dec. 20, 2018

(87) PCT Pub. No.: WO2018/004016
PCT Pub. Date: Jan. 4, 2018

(65) Prior Publication Data
US 2020/0029574 A1    Jan. 30, 2020

(51) Int. Cl.
*A01N 63/30* (2020.01)
*C12N 1/14* (2006.01)
*A01N 25/00* (2006.01)
*C12R 1/645* (2006.01)
*A01N 63/32* (2020.01)

(52) U.S. Cl.
CPC .............. *A01N 63/30* (2020.01); *A01N 25/00* (2013.01); *A01N 63/32* (2020.01); *C12N 1/14* (2013.01); *C12R 1/645* (2013.01)

(58) Field of Classification Search
CPC ........ A01N 63/30; A01N 25/00; A01N 63/32; A01N 63/34; A01N 63/36; A01N 63/38; A01N 63/40; A01N 63/50; A01N 63/60; C12N 1/14; C12R 1/645
See application file for complete search history.

(56) References Cited

U.S. PATENT DOCUMENTS

2011/0028500 A1  2/2011  Su et al.
2011/0257009 A1  10/2011  Seitz et al.

FOREIGN PATENT DOCUMENTS

| JP | 2010215593 | 9/2010 |
| JP | 2011182660 | 9/2011 |
| KR | 1020010069238 | 7/2001 |
| KR | 1020090105726 | 10/2009 |
| KR | 1020120047985 | 5/2012 |
| KR | 1020120075936 | 7/2012 |
| KR | 1020130057994 | 6/2013 |
| KR | 1020160080224 | 7/2016 |

OTHER PUBLICATIONS

International Search Report and Written Opinion of the International Searching Authority with English language translation corresponding to International Patent Application No. PCT/KR2016/006818, dated Mar. 27, 2017 (5 pages).
Shen et al. "Root Colonizig and Biocontrol Competency of Serratia plymuthica A21-4 against Phytophthora Blight of Pepper" The Plant Pathology Journal 21(1):64-67 (2005).
Extended European Search Report corresponding to EP 16907381.4, dated Oct. 25, 2019 (29 pp).
Morita et al. "Isolation of *Pseudozyma churashimaensis* sp. nov., a novel ustilaginomycetous yeast species as a producer of glycolipid biosurfactants, mannosylerythritol lipids" Journal of Bioscience and Bioengineering, 112 (2):137-144 (2011).
Barda et al. "Pseudozyma aphidis Induces Salicylic-Acid-Independent Resistance to Clavibacter michiganensis in Tomato Plants" The American Phytopathological Society, 99(5):621-626 (2015).

*Primary Examiner* — John Pak
*Assistant Examiner* — Andriae M Holt
(74) *Attorney, Agent, or Firm* — Myers Bigel, P.A.

(57) ABSTRACT

The present invention provides a strain of *Pseudozyma churashimaensis* RGJ1, which is isolated from a pepper plant and leads to induced systemic resistance against plant pathogens or plant viruses; a microbial preparation for controlling plant diseases or increasing plant yields, including, as an active ingredient, the strain or a culture thereof; a method for preparing the microbial preparation, including a step of culturing the strain; and a method for controlling plant diseases, including a step of performing dipping treatment, soil drenching treatment or spraying treatment onto aerial foliage for a plant seedling with the strain or the culture thereof.

9 Claims, 6 Drawing Sheets
Specification includes a Sequence Listing.

[Figure 1]

| Isolates(Rm) | ITS sequence |
|---|---|
| RGJ1 (GEOJE) | *Pseudozyma churashimaensis* |
| RGJ2 | *Pseudozyma aphidis* strain HX6610 |
| RGJ3 | *Pseudozyma aphidis* strain HX6610 |
| RGJ4 | *Sporidiobolus* sp. CanS-79 |
| RGJ5 | *Cryptococcus magnus* strain AUMC 7772 |
| RGS11 (GOSEONG) | *Pseudozyma aphidis* strain JCM 10318 |
| RGS12 | *Pseudozyma aphidis* strain HX6610 |
| RGS13 | *Pseudozyma tsukubaensis* |
| RGS14 | *Pseudozyma aphidis* strain JCM 10318 |
| RGS15 | *Jaminaea* sp. NYNU 12726 |
| RHY1 (HAMYANG) | *Sporobolomyces* sp. YR-1 |
| RHY2 | *Plectosphaerella alismatis* strain CBS |
| RHY3 | *Cryptococcus aureus* strain G7a |
| RSC1 (SUNCHEON) | *Pseudozyma aphidis* isolate NH73 |
| RSC2 | *Pseudozyma aphidis* strain JCM 10318 |
| RSC3 | *Pseudozyma aphidis* strain JCM 10318 |
| RSC4 | *Sporobolomyces* sp. YR-1 |

[Figure 2]

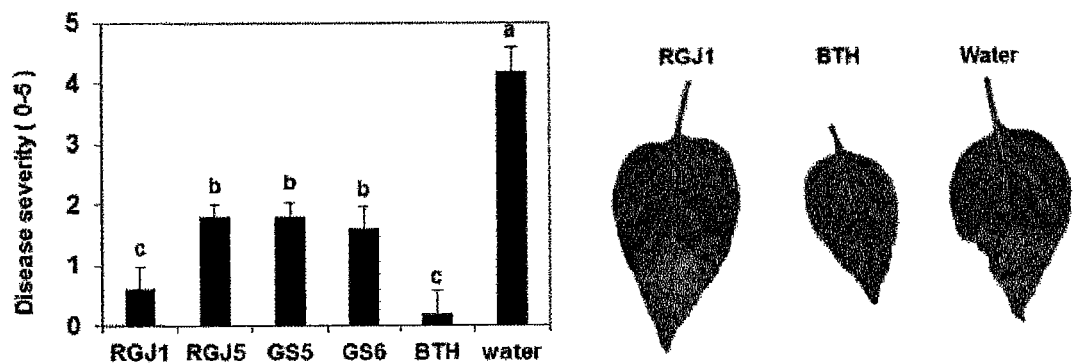

[Figure 3]
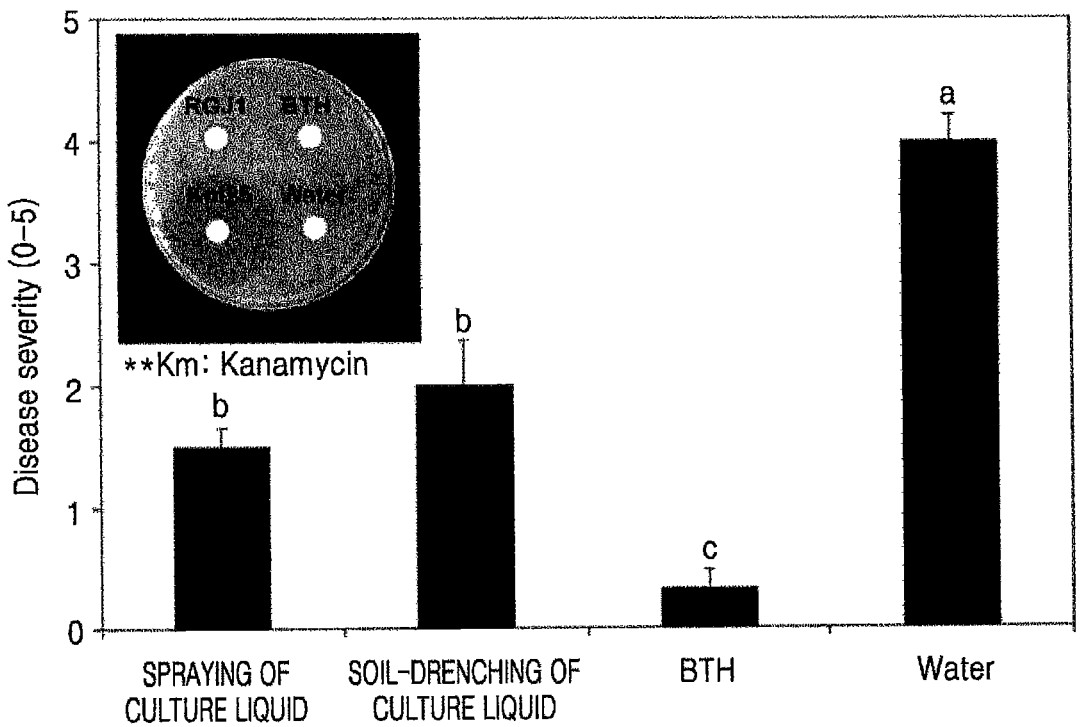
[Figure 4]
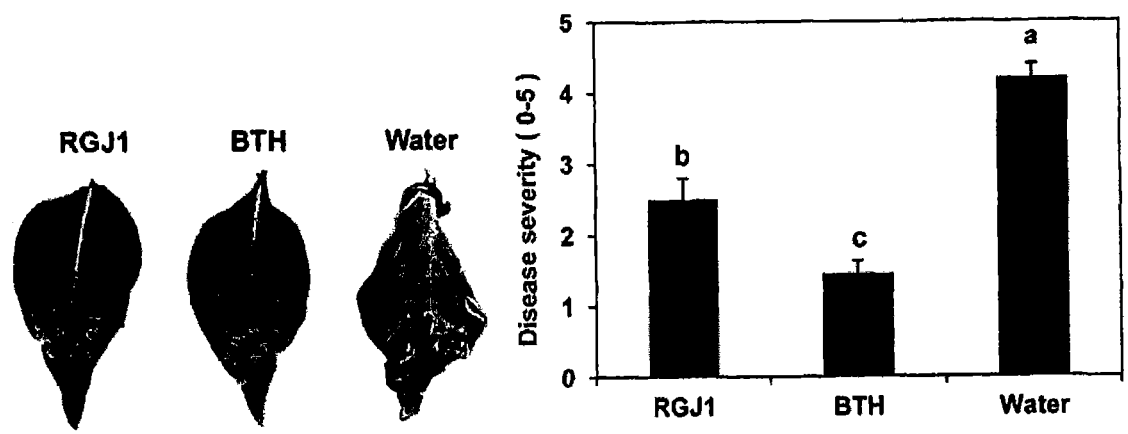

[Figure 5]
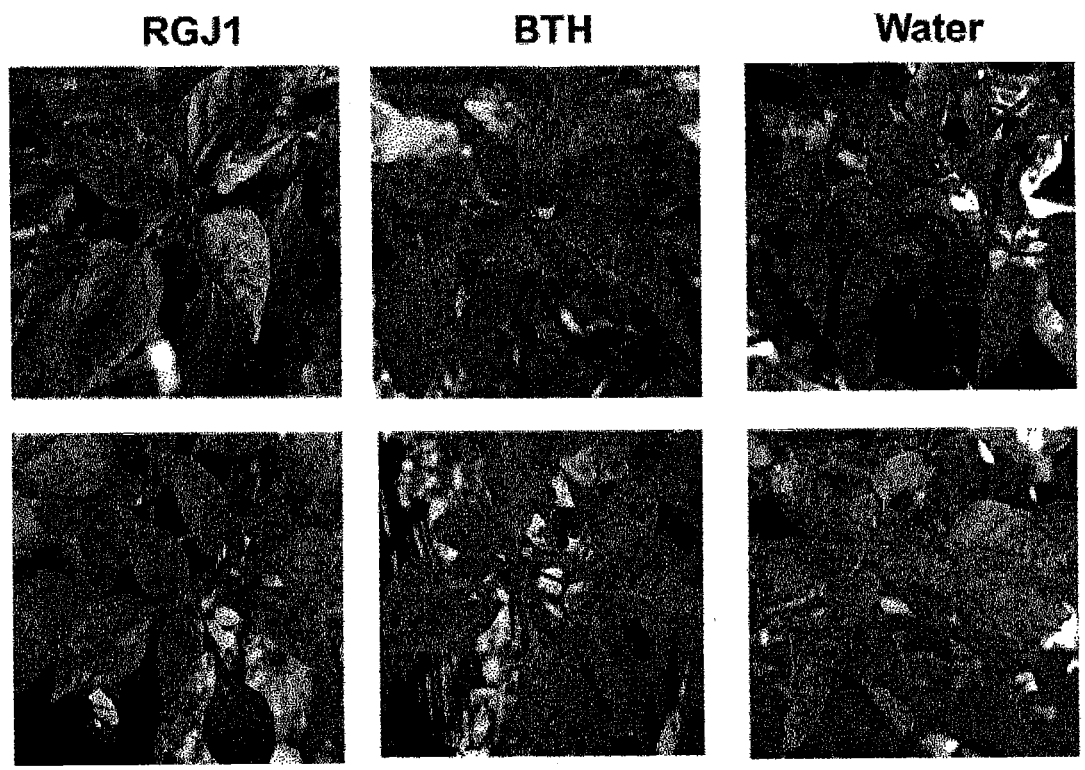
[Figure 6]
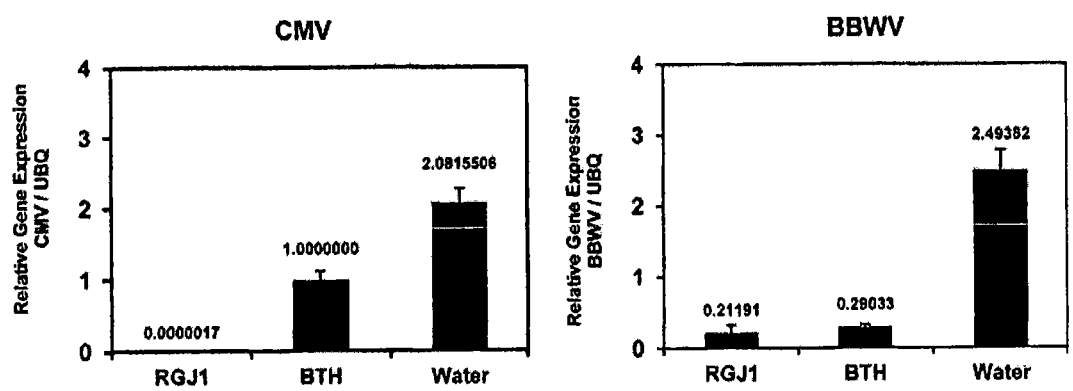
** DATA LABEL    RELATIVE EXPRESSION LEVEL

[Figure 7]
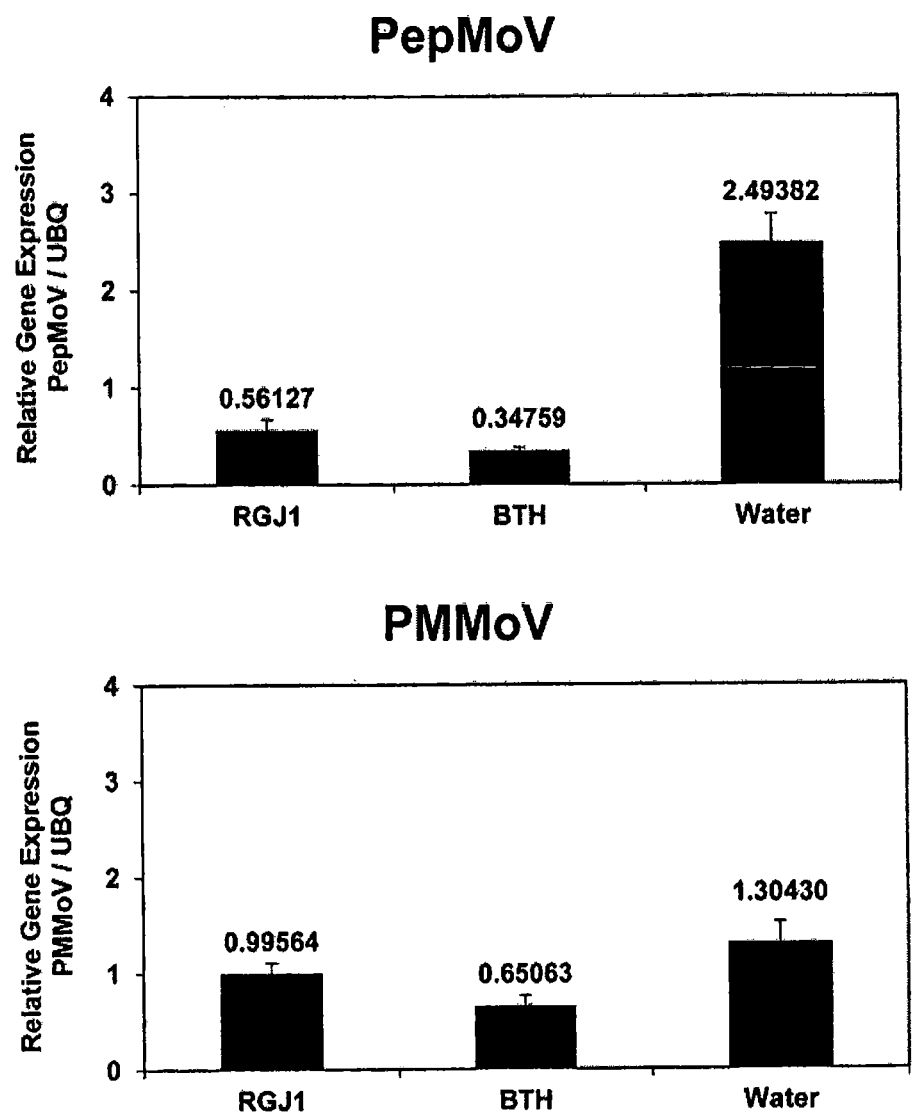

[Figure 8]
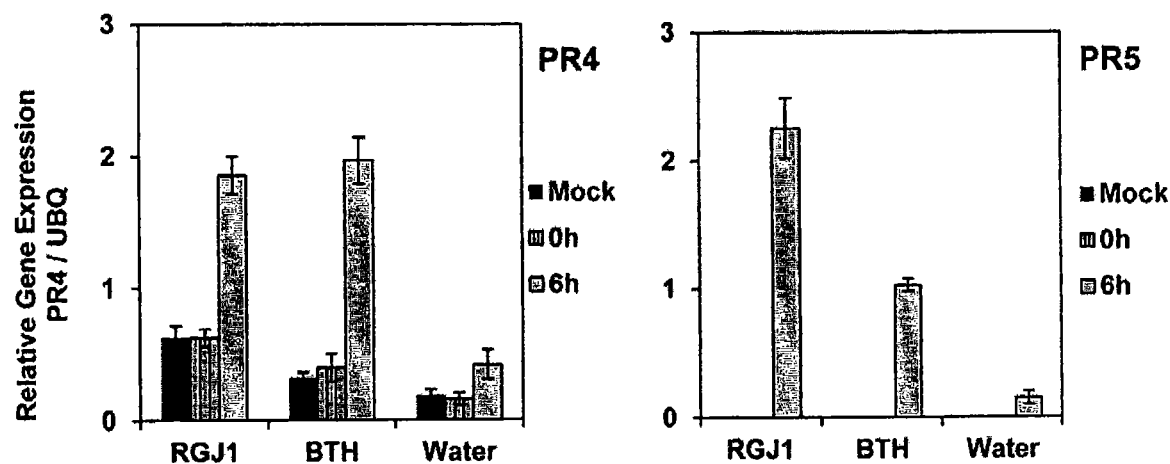
[Figure 9]
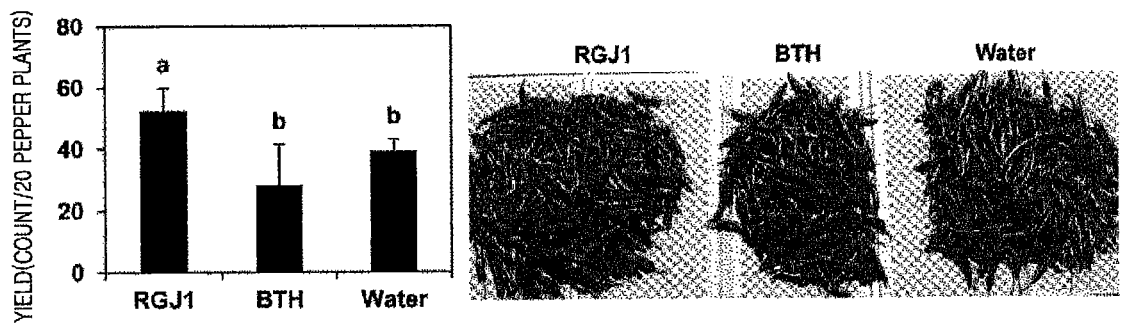

[Figure 10]
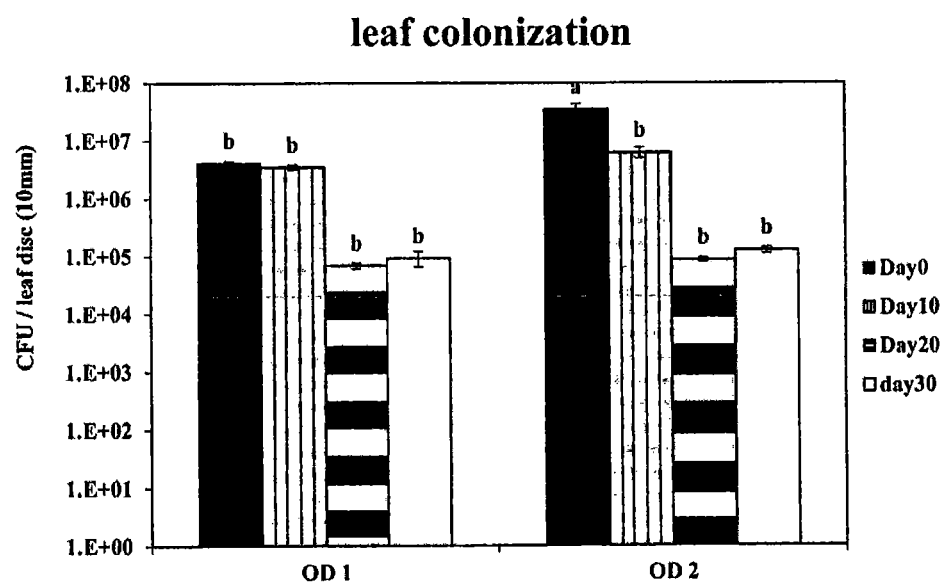

PSEUDOZYMA CHURASHIMAENSIS STRAIN RGJ1 ISOLATED FROM PEPPER PLANT AND USE THEREOF

CROSS REFERENCE TO RELATED APPLICATIONS

This application is a 35 U.S.C. § 371 national stage application of PCT International Application No. PCT/KR2016/006818, filed Jun. 27, 2016, the contents of which are incorporated herein by reference in its entirety. The above-referenced PCT International Application was published in the Korean language as International Publication No. WO 2018/004016 A1 on Jan. 4, 2018.

STATEMENT REGARDING ELECTRONIC FILING OF A SEQUENCE LISTING

A Sequence Listing in ASCII text format, submitted under 37 C.F.R. § 1.821, entitled 1433-19 _ST25.txt, 2,783 bytes in size, generated on Sep. 23, 2019 and filed via EFS-Web, is provided in lieu of a paper copy. This Sequence Listing is incorporated by reference into the specification for its disclosures.

TECHNICAL FIELD

The present invention relates to a strain of *Pseudozyma churashimaensis* RGJ1, which is isolated from a pepper plant and leads to induced systemic resistance against plant pathogens or plant viruses; a microbial preparation for controlling plant diseases or increasing plant yields, including, as an active ingredient, the strain or a culture thereof; a method for preparing the microbial preparation, including a step of culturing the strain; and a method for controlling plant diseases, including a step of performing dipping treatment, soil drenching treatment or spraying treatment onto aerial foliage for a plant seedling with the strain or the culture thereof.

BACKGROUND ART

Currently, a method mainly used for inhibiting generation of and controlling plant pathogenic bacteria is to use chemically synthesized pesticides. However, these synthetic pesticides destroy ecosystems, and cause human toxicity problems due to residues thereof. As a result, a possibility of causing various diseases such as cancer, malformation and the like is very high, and, thus, the use thereof is limited. Therefore, research on the development of environmentally friendly biological pesticides capable of replacing the chemical synthetic pesticides is actively underway. One of the methods that has been tried by many researchers to solve the problems of the chemical control method is a biological control method using microorganisms. The biological control method using the microorganisms has been studied as an alternative to the chemical control method for controlling diseases of crops as, recently, consumers' awareness of food safety has increased and preference for environmentally friendly agricultural products has increased rapidly.

Important diseases of pepper include anthracnose, powdery mildew, a bacterial spotty disease, and viral diseases which occur in the aerial portion, including pepper late blight as a soil infectious disease. These have been known as economically critical diseases that threaten the production of peppers. Since not only the cultivation period of the pepper is long, but also the patterns of the pepper disease are very different according to the change of the weather. It is difficult to control the disease of the pepper. In this regard, the pepper is one of the crops that have been much frequently treated with the bactericide during the cultivation period. Therefore, in order to produce environment-friendly clean pepper, it is necessary to utilize the microorganisms for disease control, which are selected to have an excellent disease control effect. Most of the microorganisms developed to control pepper disease have been developed for controlling pepper late blight. *Serratia plymuthica* has been reported to be effective in controlling the pepper late blight (Shen et al., Plant Pathol, J., 21, 64-67, 2005). However, there are few reports of microorganisms that have an excellent control effect against the disease of aerial portion of the pepper.

Korean Patent Application Publication No. 2009-0105726 discloses "*Bacillus megaterium* isolate 22-5 controlling bacterial spot and anthracnose of red-pepper". Korean Patent Application Publication No. 2012-0075936 discloses "*Bacillus* sp. PB25 strain isolated from soil and uses thereof". Beyond the prokaryotic bacteria, the above patent documents fail to disclose a eukaryotic yeast strain of *Pseudozyma churashimaensis* RGJ1 in accordance with the present invention, which is isolated from a pepper plant and leads to induced systemic resistance against plant pathogens or plant viruses.

DETAILED DESCRIPTION OF THE INVENTION

Technical Problem

The present invention is derived from the above requirements. The present invention was completed by confirming that *Pseudozyma churashimaensis* strain RGJ1, isolated and identified from a pepper leaf leads to induced systemic resistance against bacterial pathogens or plant viruses of pepper plants and thus has a plant disease control effect.

Technical Solution

In one aspect of the present invention, there is provided *Pseudozyma churashimaensis* strain RGJ1 isolated from a pepper plant, in which the strain of *Pseudozyma churashimaensis* RGJ1 leads to induced systemic resistance against a plant pathogen or plant virus.

In another aspect of the present invention, there is provided a microbial preparation for controlling a plant disease, in which the preparation includes, as an active ingredient, *Pseudozyma churashimaensis* strain RGJ1 or a culture thereof.

In still another aspect of the present invention, there is provided a microbial preparation for increasing a yield of a plant, in which the preparation includes, as an active ingredient, the *Pseudozyma churashimaensis* strain RGJ1 or a culture thereof.

In still another aspect of the present invention, there is provided a method for preparing a microbial preparation, the method comprising culturing the *Pseudozyma churashimaensis* strain RGJ1.

In still another aspect of the present invention, there is provided a method for controlling a plant disease, the method comprising performing treatment on a plant seedling with the *Pseudozyma churashimaensis* strain RGJ1 or a culture thereof, in which the treatment includes dipping treatment, soil drenching treatment or spraying treatment onto aerial foliage.

Advantageous Effects

It was confirmed that the present *Pseudozyma churashimaensis* strain RGJ1 isolated and identified from a pepper leaf leads to induced systemic resistance against bacterial pathogens or plant viruses of pepper plants and thus has a plant disease control effect. The strain according to the present invention may eliminate the risk of environmental pollution as caused by the side effects of chemical pesticides and human toxicity due to residual pesticides and thus may be used as an eco-friendly plant protectant. The strain according to the present invention has an effect of controlling infectious bacterium on the pepper plant and of increasing a disease resistance of the plant, and thus may be industrially useful.

BRIEF DESCRIPTION OF DRAWINGS

FIG. 1 illustrates species of yeast isolated from regions and regions of sampling to isolate viable yeast from a pepper.

FIG. 2 illustrates results of a primary analysis of induced resistance to yeast strains surviving in a pepper: RGJ1: *Pseudozyma churashimaensis*, RGJ5: *Cryptococcus magnus*, GS5: *Pseudozyma aphidis*, GS6: *Pseudozyma tsukubaensis*.

FIG. 3 illustrates results of a secondary analysis of induced resistance to RGJ1 as a yeast strain isolated from a pepper. BTH (benzothiadiazole): induced resistance positive control, Kanamycin: direct bacteria killing agent (a broad spectrum antibiotic).

FIG. 4 illustrates a result of checking an induced resistance of a pepper treated with a yeast RGJ1 according to the present invention in a field against a bacterial spot pathogen, *X. axonopodis* pv. *vesicatoria*.

FIG. 5 illustrates a result of checking, via a symptom, an induced resistance of a pepper treated with a yeast RGJ1 according to the present invention in a field against a virus.

FIG. 6 illustrates a result of checking, via a quantity measurement of virus using qRT-PCR, an induced resistance of a pepper treated with a yeast RGJ1 according to the present invention in a field against a virus. CMV: Cucumber Mosaic Virus, BBWV: Broad Bean Wilt Virus.

FIG. 7 illustrates a result of checking, via a quantity measurement of virus using qRT-PCR, an induced resistance of a pepper treated with a yeast RGJ1 according to the present invention in a field against a virus. PepMoV: Pepper Mottle Virus, PMMoV: Pepper Mild Mottle Virus.

FIG. 8 illustrates results of analysis of expression levels of pepper PR4 and PR5, as genes related to an induced resistance of a pepper treated with a yeast RGJ1 according to the present invention against a pathogen infestation under field condition.

FIG. 9 illustrates an increase in a pepper yield via treatment with a yeast RGJ1 according to the present invention in a field.

FIG. 10 illustrates a result of checking an ability of a yeast RGJ1 to colonize on the leaf in the greenhouse.

BEST MODE

In order to achieve the object of the present invention, there is provided a strain of *Pseudozyma churashimaensis* RGJ1 isolated from a pepper plant, in which the strain of *Pseudozyma churashimaensis* RGJ1 leads to induced systemic resistance against a plant pathogen or plant virus. The *Pseudozyma churashimaensis* RGJ1 was deposited on Jun. 24, 2016, at the Korea Research Institute of Bioscience and Biotechnology (Accession No. KCTC13051BP).

In the strain according to one embodiment according to the present invention, the plant pathogen or plant virus may be a pathogen or virus of various plants. Preferably, in the strain according to one embodiment according to the present invention, the plant pathogen or plant virus may be, but is not limited to, a pepper plant pathogen or a pepper plant virus. The plant pathogen may be a bacterial pathogen, preferably a causative bacterium of a pepper bacterial spot. More preferably, the bacterial pathogen may be *Xanthomonas axonopodis* pv. *vesicatoria* but may not be limited thereto. The pepper plant virus may include Cucumber Mosaic Virus (CMV), Tobacco Mosaic Virus (TMV), Broad Bean Wilt Virus (BBWV), *Chrysanthemum* Mild Mottle Virus (CMMV), Potato Virus Y (PVY), Tomato Spotted Wilt Virus (TSWV), Pepper Mottle Virus (PepMoV), Pepper Mild Mottle Virus (PMMoV), and so on. Preferably, the pepper plant virus may be the Cucumber Mosaic Virus (CMV), Broad Bean Wilt Virus (BBWV), Pepper Mottle Virus (PepMoV), Pepper Mild Mottle Virus (PMMoV), and the like but may not be limited thereto.

This deposit was made under the provisions of the Budapest Treaty on the International Recognition of the Deposit of Microorganisms for the Purposes of Patent Procedure and the Regulations there under (Budapest Treaty). All restrictions on the availability to the public of the material so deposited will be irrevocably removed upon the granting of a patent. Applicant assures availability of the progeny to one determined by the U.S. Commissioner of Patents and Trademarks to be entitled thereto according to 35 USC §122 and the Commissioner's rules pursuant thereto (including 37 CFR §1.14). Availability of the deposited biological material is not to be construed as a license to practice the invention in contravention of the rights granted under the authority of any government in accordance with its patent laws.

In another aspect of the present invention, there is provided a microbial preparation for controlling a plant disease, in which the preparation includes, as an active ingredient, the *Pseudozyma churashimaensis* strain RGJ1 or a culture thereof. The plant disease may be caused by plant pathogen or plant virus. Preferably, the plant disease may be caused by pepper plant pathogen or pepper plant virus. The present invention is not limited thereto. The pepper plant pathogen or pepper plant virus is as described above.

The microbial preparation for controlling the plant disease may include, as an active ingredient, the *Pseudozyma churashimaensis* strain RGJ1 or a culture thereof, in which the strain is isolated from a pepper plant, in which the *Pseudozyma churashimaensis* strain RGJ1 leads to induced systemic resistance against a plant pathogen or plant virus. The microbial preparation according to the present invention may be prepared in a liquid fertilizer form. The microbial preparation may be used in a powder form by adding an extender to the microbial preparation. The microbial preparation may be formulated and granulated. However, the formulation is not particularly limited. In other words, in an environmentally friendly organic farming where a chemical fertilizer supply is limited, the microbial preparation may be formulated as a biological fertilizer to overcome such a limitation.

In still another aspect of the present invention, there is provided a microbial preparation for increasing a yield of a plant, in which the preparation includes, as an active ingredient, the *Pseudozyma churashimaensis* strain RGJ1 or a culture thereof. The plant may be, but is not limited to, a pepper plant. When the pepper plant was treated with the strain according to the present invention, the pepper fruit yield was increased by about 30% compared to a control with no treatment.

In still another aspect of the present invention, there is provided a method for preparing a microbial preparation, the method including culturing the *Pseudozyma churashimaensis* strain RGJ1. The yeast strain may be cultured by any method known in the art and may be not limited to a specific method.

In still another aspect of the present invention, there is provided a method for controlling a plant disease, the method including performing treatment on a plant seedling with the *Pseudozyma churashimaensis* strain RGJ1 or a culture thereof, in which the treatment includes dipping treatment, soil drenching treatment or spraying treatment onto aerial foliage or soil belowground. The plant disease may be caused by plant pathogen or plant virus. Preferably, the plant disease may be caused by pepper plant pathogen or pepper plant virus. The present invention is not limited thereto. The pepper plant pathogen or pepper plant virus is as described above.

The method for controlling the plant diseases may include performing treatment including dipping treatment, soil drenching treatment or spraying treatment onto aerial foliage on a plant seedling with the *Pseudozyma churashimaensis* strain RGJ1, a culture thereof or a microbial preparation using the strain. In the case of the dipping treatment, the culture medium and microbial preparation may be poured into the soil around the plant, or plant seeds may be immersed in the culture medium and formulation.

Hereinafter, the present invention is illustrated in detail with reference to Examples. However, the present examples are merely examples of the present invention, and the content of the present invention is not limited to the presenting examples.

Example 1. Isolation of Yeast Strains Surviving on Pepper

To isolate yeasts that play a useful role in pepper and survive on pepper leaves, pepper leaves were collected from Chungcheongnam-do and Jeollado. From September to November 2013, the leaves of the middle portion of the pepper at the end of harvest thereof were collected in Geoje, Goseong, Hamyang, Jinan, Namhae and Suncheon, etc. The collected leaves were cut into a circular disk shape with a cork borer of 10 mm in a diameter. Three disc-like leaves were placed in a 1.5 ml tube containing 1 ml of sterilized water. Beads (zirconia beads (small beads having a diameter of 1 mm)) were put in the tube. Vortexing was performed using the beads for a sufficient period of time to allow for better isolation of the microorganisms attached on the leaf surface. The state in which the leaf disc first enters was considered to be undiluted. The undiluted solution was sequentially diluted to $\frac{1}{10}$ and $\frac{1}{100}$, etc. 100 μl of each diluted solution was smeared on an agar plate medium. The agar medium as used was prepared by adding rifampicin (rifampin capsule; Yuhan Pharmaceutical Company) (final concentration 100 μg/ml) as an antibiotic preventing bacteria from growing, onto a YPD medium as a yeast-dedicated medium to isolate only yeast cells. Yeast colonies isolated from the diluted and smeared plates were separately sub-cultured, and raised into pure single cells. ITS sequencing of the single cells was directly commissioned to Xenotech. Sequences of the ITS sequencing primers as used are as follows: (ITS1 (forward direction): 5'-TCC GTA GGT GAA CCT TGC GG-3' (SEQ ID NO: 1), ITS4 (reverse direction): 5'-TCC TCC GCT TAT TGA TAT GC-3' (SEQ ID NO: 2).

Thereafter, pepper leaves were collected from the pepper fields in Jeollado, Geoje, Goseong, Hamyang, Jinan, Namhae, Suncheon. The yeasts were identified via sequencing of the isolated yeast from the harvested leaves. Various yeasts were alive on a leaf of the pepper. Among them, a yeast of *Pseudozyma* genus was dominant and a large amount of yeast thereof was survived on the pepper leaf (see FIG. 1).

Example 2. Primary Analysis of Induced Resistance of Yeast Strain Surviving in Pepper In order to confirm the induced resistance ability of the isolated yeast, a primary strain selection experiment was conducted in the greenhouse. The present inventors planted a 7-day-old pepper (new PR pepper: Hongnong seedling) in a 50-hole pot. Three weeks later, when except for cotyledons, the four true leaves came out, the present inventors sprayed the isolated yeast strain on the aerial portion of the pepper seedlings. The microorganisms treated at this time were made as follows: yeast cells grown in a solid medium for 3 days were suspended in sterilized water, and a concentration of the cells was adjusted to O.D.600=1 ($10^6$ CFU/ml). Then, 50 ml of suspension was sprayed on each pepper seedling. Seven days after the microbial treatment, the concentration of *Xanthomonas axonopodis* pv. *vesicatori* of the pepper was adjusted to O.D.600=0.01, and, then, *Xanthomonas axonopodis* pv. *vesicatori* was injected and inoculated directly into the backside of the pepper leaf, using a syringe. The pathogen was inoculated on three leaves per pepper seedling. After 5 to 7 days thereafter, symptoms began to appear. At this time, the induced resistance to the pathogen was confirmed by investigating the above-mentioned symptoms. The symptom investigation was conducted by arbitrarily classifying disease severity from 0 to 5 in the leaf part inoculated with the pathogenic bacteria: (0: no symptom at all; 1: a leaf turns greenish slightly opaquer than an original color; 2: yellowing of the leaf is visible; 3: the yellow part shows a little black part; 4: more than $\frac{1}{3}$ of the leaves are blackened; 5: all the leaves turn black). Four leaves per pepper seedling were individually examined. A total of 20 leaves were identified via 5 times repetitions.

The symptom was examined 7 days after the pathogen inoculation. From the examination results, *Pseudozyma churashimaensis* RGJ1 yeast, that is, the yeast isolated from Geojedo showed the most excellent disease resistance effect. This yeast treatment showed 70% symptom reduction as compared with the water control. This showed the same significance as a chemical BTH control as a positive control (see FIG. 2).

Example 3. Secondary Analysis of Induced Resistance of Yeast Strains Isolated from Pepper For the strain of *Pseudozyma churashimaensis* RGJ1, which is the most effective strain among the several isolated yeast strains used in the primary induced resistance assay, a difference in induced resistance based on the change of treatment method was confirmed. The culture medium in which yeast RGJ1 was cultured was adjusted to O.D.600=1. Under the same experimental conditions as the first induced resistance experiment, a difference in resistance was compared between when the culture medium was sprayed on the leaf surface of the aerial portion of the pepper and when the culture was directly trenched in the soil into the root of the pepper. As a positive control, BTH, a chemical that induces an induced resistance, and a water control, as a negative control, were used. The experiment proceeded in the greenhouse. Further, in order to confirm whether there is a direct sterilization action by the yeast RGJ1, the pepper bacterial spot pathogen Xav. was adjusted to O.D.600=0.5 and the Xav. was smeared into a plate with a diameter of 90 mm. Then, a paper disk having a diameter of 10 mm was disposed on the plate. Then, treatments with the yeast RGJ1 (concentration adjusted to O.D.600=1 and amount being 20 microliters), BTH (1 mM), antibiotic kanamycin 25, and water were performed in the same amounts. The treated product was then cultured at 30° C. The effects thereof were compared by observing the clear zone where bactericidal effects appeared (see FIG. 3).

The disease resistance was induced with a similar result to the results of the primary resistance test. There were no differences in the effects between the spraying treatment on the leaves and the direct soil drenching. Further, from the results of the replacement culture, there was no transparent ring around the yeast RGJ1. As a result, it was confirmed that the yeast RGJ1 did not have a sterilizing effect directly killing the pathogen and had an effect of inducing the resistance (see FIG. 3).

Example 4. Identification of Induced Resistance Against Bacterial Spotty Pathogen, as Induced from Pepper Treated with Yeast RGJ1 According to the Present Invention in Field For the yeast strains selected via the identification in the laboratory and the greenhouse, an induced resistance ability thereof was verified in a pepper field. The verification test was carried out in a pepper field of 200 pyeong area located in Oebuli, Geonbuk-myeon, Geumsan-gun, Chungcheong-nam-do (36° 8'50.81" N, 127° 29'29.20"E). On June, 2014, the strain of yeast RGJ1 was sprayed onto the aerial portion of one-month-old pepper transplanted into the field at a concentration of O.D.600=1 ($10^7$ CFU/ml) under the same experimental conditions as in the greenhouse experiment. As a positive control, BTH having an induced resistance effect was sprayed onto the aerial portion of the pepper at a concentration of 1 mM. Water treatment as a negative control was performed. In randomized treatment units, a furrow length of one treatment unit was 8 meters. The distance between the pepper and pepper was 40 cm. One treatment unit contained 20 pepper plants. Two liters of each of the culture and control material were treated per treatment unit. Four repetition experiments were performed in randomly divided treatment units. Ten days after the treatment, the bacterial spotty pathogen, i.e., *Xanthomonas axonopodis* pv. *vesicatoria* was diluted to O.D.600=0.01. The diluted bacterial spotty pathogen was inoculated into the pepper through the back of the leaf using a syringe. Five leaves were inoculated per a single pepper plant. A total of 10 pepper plants were inoculated per a single treatment unit. After 7 days, symptom was observed. The severity of the disease was determined by dividing the severity of the symptom into 0 to 5 levels in the same way as in the greenhouse identification experiment.

From the field test results, it was confirmed that the resistance was induced via spray treatment of the yeast in the same manner as in the greenhouse experiment, and the symptom of bacterial spotty disease was reduced by 50% (see FIG. 4).

Example 5. Identification of Induced Resistance Against Virus of Pepper Treated with Yeast RGJ1 According to the Present Invention in Field 5 fresh young leaves were collected from the pepper that had passed 60 days after yeast treatment in the outdoor field experiment. The leaves were immediately put into liquid nitrogen and rapidly frozen. Thereafter, the leaf was ground using a mortar. From the pulverized or ground leaves, RNA was extracted using an RNA extraction kit (RNeasy kit; QIAGEN). The extracted RNA was synthesized into cDNA. RT-qPCR, as a method for quantifying the amount of virus, was performed on the synthesized cDNA using qPCR (CFX connect Real-Time System; BIO-RAD).

The degree of infection was quantified using naturally occurring CMV (Cucumber Mosaic Virus) and BBWV (Broad Bean Wilt Virus)-specific primers. The conditions of qPCR and the primers used are as follows. CMV coat protein forward direction: 5'-CGTTGCCGCTATCTCTGCTAT-3' (SEQ ID NO.: 3), CMV coat protein reverse direction: 5'-GGATGCTGCATACTGACAAACA-3' (SEQ ID NO.: 4), BBWV forward direction: 5'-AATGAAGTGGTGCT-CAACTACACA-3' (SEQ ID NO.: 5), BBWV reverse direction: 5'-TTTTGGAGCATTCAACCATTTGGA-3' (SEQ ID NO.: 6). Further, using PepMoV (Pepper Mottle Virus) and PMMoV (Pepper Mild Mottle Virus)-specific primers, the degree of infection was quantified. The conditions of qPCR and the primers used are as follows. PepMoV forward direction: 5'-AAGATCAGACACATGGA-3' (SEQ ID NO.: 7), PepMoV reverse direction: 5'-CAAGCAAGGGTATG-CATGT-3' (SEQ ID NO.: 8), PMMoV forward direction: 5'-ACAGTTTCCAGTGCCAATCA-3' (SEQ ID NO.: 9), PMMoV reverse direction: 5'-AAGCGTCTCGGCAGTTG-3' (SEQ ID NO.: 10).

TABLE 1

| qPCR condition | |
|---|---|
| 1 | 95.0 C for 10:00 |
| 2 | 95.0 C for 0:30 |
| 3 | 55.0 C for 0:30 |
| 4 | 72.0 C for 0:30 |
| | + Plate Read |
| 5 | GOTO 2. 44 more times |
| 6 | 72.0 C for 1:00 |
| 7 | 45.0 C for 0:30 |
| | END |

In the virus symptom survey, from the results of comparing the new leaves of pepper between the water control and the yeast treatment, it was confirmed that in the water control, virus symptoms are severe, while in the yeast treatment, the symptom was weak (see FIG. 5). Further, from the results of quantification of virus using qPCR, for both the representative CMV and BBWV viruses, the amount of virus was reduced by 10 times in the yeast treatment compared to the water control. Thus, it was confirmed that the pepper plants were infected with less virus by the yeast treatment (see FIG. 6). Further, for both viruses, PepMoV and PMMoV, pepper plants were found to be less vulnerable to the virus infection by the yeast treatment (see FIG. 7).

Example 6. Analysis of Expression Levels of Genes Related to an Induced Resistance of a Pepper Treated with a Yeast RGJ1 According to the Present Invention Against a Pathogen Infestation In order to investigate the gene expression level for studying the mechanism of action of yeast, in inoculating the bacterial spotty pathogen during the field experiment, at following three time points: ① before inoculation of the pathogen ② immediately after the inoculation of the pathogen ③ at 6 hours after the inoculation of the pathogen, the pepper leaves were collected. The leaves were then fed and rapidly frozen in liquid nitrogen. In the same manner as in the virus quantitation method, RNA is extracted from the leaf, and RNA was synthesized into cDNA. Then, the expression level of the gene related to the induced resistance of the pepper was examined using qPCR. Specifically, expression of PR gene as a representative gene related to the induced resistance of pepper was confirmed. The conditions of qPCR are the same as in the above virus quantification method. Information on the primer used is as follows. CaPR4 forward direction: 5'-AACTGGGATTT-GAGAACTGCCAGC-3' (SEQ ID NO.: 11), reverse direction: 5'-ATCCAAGGTACATATAGAGCTTCC-3' (SEQ ID NO.: 12), CaPR5 forward direction: 5'-CTC-CACAAGAAACAAGGCA-3' (SEQ ID NO.: 13), reverse direction: 5'-GTACGAAGCACGCACACAA-3' (SEQ ID NO.: 14).

In the yeast treatment, the expression levels of the resistance genes PR4 and PR5 were significantly increased after 6 hours. This resulted in a resistance priming effect, leading to a faster response time to pathogen invasion (see FIG. 8).

Example 7. Investigation of Yield of Pepper in Field According to Treatment of Yeast RGJ1 According to the Present Invention After confirming the induced resistance in the field, the pepper yield in 20 pepper plants in each treatment unit was investigated. These surveys were repeated four times in total. In the treatment unit with yeast RGJ1 treatment, the yield was increased by about 30% compared to the non-treatment unit (see FIG. 9).

Example 8. Identification of Fixation Ability of RGJ1 Yeast onto Left in Greenhouse To confirm the ability of Pseudozyma churashimaensis RGJ1, a yeast strain isolated from pepper leaves, to settle on leaves, the present inventors conducted experiments on pepper seedlings in the greenhouse. Yeast suspension was inoculated at two concentrations of O.D.600=1 and 2 on the leaf of the pepper three weeks after germination. The suspension containing dispersed bacteria therein was sprayed at 50 ml on the aerial portion of the pepper. Thereafter, the leaves were sampled. The present inventors obtained three leaf discs by punching using a cork borer having a diameter of 10 mm. The disk-shaped leaves were placed in a 1.5 ml tube containing 1 ml of sterilized water. Then, vortexing was performed sufficiently using beads. The well-vortexed solution was diluted at a ⅒ concentration. The diluted solution was smeared at 100 microliters on a YPD agar plate as a yeast-dedicated medium. The number of colonies thus produced was counted to measure a CFU value. Sampling was performed every 10 days from the day of spraying (Day 0) (see FIG. 10). There was no significant difference according to the O.D.600 value at the initial spraying. It was confirmed that the yeast strains which were settled on a 10 mm leaf disk were maintained at $10^4$ or more counts in a time period from the 20th day to the 30th day since the day 0. This result indicates that the isolated yeast strain lives well on the leaf of pepper. It may be considered that the density of $10^4$ is the most appropriate growth concentration of the yeast strain. Furthermore, when the yeast strain is sprayed on the crop, the yeast strains survive well in the leaves due to its excellent ability to fix on the leaves, and an induced resistance of the crop is kept for a long period of time. Thus, the crops are resistant to bacterial or viral diseases.

[Accession Number]
Deposition Institution name: Korea Research Institute of Bioscience and Biotechnology
Accession number: KCTC13051BP
Accession date: 20160624

The invention claimed is:

1. A method for controlling a plant disease, the method comprising: spraying, dipping, and/or drenching a plant with an effective amount of a microbial preparation comprising a strain of *Pseudozyma churashimaensis* RGJ1, or a culture thereof, deposited under accession number KCTC1305BP, thereby increasing a resistance of the plant to a plant pathogen and/or a plant virus.

2. The method of claim 1, wherein the plant is a pepper plant.

3. The method of claim 1, wherein the strain of *Pseudozyma churashimaensis* RGJ1 is isolated from a pepper plant.

4. The method of claim 1, wherein the plant pathogen and/or plant virus is a pepper plant pathogen and/or a pepper plant virus.

5. The method of claim 1, wherein the spraying, dipping, and/or drenching the plant with the effective amount of the microbial preparation comprising the *Pseudozyma churashimaensis* RGJ1, or the culture thereof, increases a yield of the plant.

6. The method of claim 1, wherein the plant is a plant seedling.

7. The method of claim 1, wherein the spraying, dipping, and/or drenching the plant with the effective amount of the microbial preparation increases the resistance of the plant to at least one plant virus selected from the group consisting of Cucumber Mosaic Virus (CMV), Tobacco Mosaic Virus (TMV), Broad Bean Wilt Virus (BBWV), Chrysanthemum Mild Mottle Virus (CMMV), Potato Virus Y (PVY), Tomato Spotted Wilt Virus (TSWV), Pepper Mottle Virus (PepMoV), and Pepper Mild Mottle Virus (PMMoV).

8. The method of claim 1, wherein the plant pathogen is *Xanthomonas axonopodis* pv. *vesicatoria*.

9. The method of claim 1, wherein the spraying, dipping, and/or drenching the plant with the effective amount of the microbial preparation comprising the strain of *Pseudozyma churashimaensis* RGJ1, or the culture thereof, leads to induced systemic resistance of the plant against the plant pathogen and/or the plant virus.

* * * * *

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
tccgtaggtg aaccttgcgg                                        20

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
tcctccgctt attgatatgc                                        20

<210> SEQ ID NO 3
<211> LENGTH: 21
<212> TYPE: DNA
```

```
<213> ORGANISM: Artificial
<220> FEATURE:
<223> OTHER INFORMATION: primer

<400> SEQUENCE: 3
cgttgccgct atctctgcta t                                        21

<210> SEQ ID NO 4
<211> LENGTH: 22
<212> TYPE: DNA
<213> ORGANISM: Artificial
<220> FEATURE:
<223> OTHER INFORMATION: primer

<400> SEQUENCE: 4
ggatgctgca tactgacaaa ca                                       22

<210> SEQ ID NO 5
<211> LENGTH: 24
<212> TYPE: DNA
<213> ORGANISM: Artificial
<220> FEATURE:
<223> OTHER INFORMATION: primer

<400> SEQUENCE: 5
aatgaagtgg tgctcaacta caca                                     24

<210> SEQ ID NO 6
<211> LENGTH: 24
<212> TYPE: DNA
<213> ORGANISM: Artificial
<220> FEATURE:
<223> OTHER INFORMATION: primer

<400> SEQUENCE: 6
ttttggagca ttcaaccatt tgga                                     24

<210> SEQ ID NO 7
<211> LENGTH: 17
<212> TYPE: DNA
<213> ORGANISM: Artificial
<220> FEATURE:
<223> OTHER INFORMATION: primer

<400> SEQUENCE: 7
aagatcagac acatgga                                             17

<210> SEQ ID NO 8
<211> LENGTH: 19
<212> TYPE: DNA
<213> ORGANISM: Artificial
<220> FEATURE:
<223> OTHER INFORMATION: primer

<400> SEQUENCE: 8
caagcaaggg tatgcatgt                                           19

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
acagtttcca gtgccaatca                                          20
```

-continued

```
<210> SEQ ID NO 10
<211> LENGTH: 17
<212> TYPE: DNA
<213> ORGANISM: Artificial
<220> FEATURE:
<223> OTHER INFORMATION: primer

<400> SEQUENCE: 10
aagcgtctcg gcagttg                                                    17

<210> SEQ ID NO 11
<211> LENGTH: 24
<212> TYPE: DNA
<213> ORGANISM: Artificial
<220> FEATURE:
<223> OTHER INFORMATION: primer

<400> SEQUENCE: 11
aactgggatt tgagaactgc cagc                                            24

<210> SEQ ID NO 12
<211> LENGTH: 24
<212> TYPE: DNA
<213> ORGANISM: Artificial
<220> FEATURE:
<223> OTHER INFORMATION: primer

<400> SEQUENCE: 12
atccaaggta catatagagc ttcc                                            24

<210> SEQ ID NO 13
<211> LENGTH: 19
<212> TYPE: DNA
<213> ORGANISM: Artificial
<220> FEATURE:
<223> OTHER INFORMATION: primer

<400> SEQUENCE: 13
ctccacaaga aacaaggca                                                  19

<210> SEQ ID NO 14
<211> LENGTH: 19
<212> TYPE: DNA
<213> ORGANISM: Artificial
<220> FEATURE:
<223> OTHER INFORMATION: primer

<400> SEQUENCE: 14
gtacgaagca cgcacacaa                                                  19
```